(12) United States Patent
Suen

(10) Patent No.: US 8,418,302 B1
(45) Date of Patent: Apr. 16, 2013

(54) TOOTH BRUSH MOTOR

(76) Inventor: Chi Ming Suen, Kowloon (HK)

( * ) Notice: Subject to any disclaimer, the term of this patent is extended or adjusted under 35 U.S.C. 154(b) by 267 days.

(21) Appl. No.: 12/821,764

(22) Filed: Jun. 23, 2010

(51) Int. Cl.
*A46B 13/00* (2006.01)
*A47L 11/00* (2006.01)

(52) U.S. Cl.
USPC .................................. 15/22.2; 310/36; 310/50

(58) Field of Classification Search .......... 15/22.1–22.4, 15/23; 310/36–39, 50, 156.01–156.84, 40; H02K 33/16; A46B 13/00; A47L 11/00
See application file for complete search history.

(56) References Cited

U.S. PATENT DOCUMENTS

| | | | |
|---|---|---|---|
| 6,700,230 B1 * | 3/2004 | Gokturk | 310/12.15 |
| 7,218,018 B2 * | 5/2007 | Hasegawa et al. | 310/12.33 |
| 7,315,098 B2 * | 1/2008 | Kunita et al. | 310/15 |
| 7,443,059 B2 * | 10/2008 | Kobayashi et al. | 310/12.04 |
| 2005/0127759 A1 * | 6/2005 | Kraus et al. | 310/36 |
| 2006/0168745 A1 * | 8/2006 | Kobayashi et al. | 15/22.1 |
| 2006/0255665 A1 * | 11/2006 | Kraus et al. | 310/36 |
| 2007/0011834 A1 * | 1/2007 | Shimizu et al. | 15/22.1 |
| 2008/0185922 A1 * | 8/2008 | Kressner et al. | 310/36 |
| 2008/0258566 A1 * | 10/2008 | Shimizu et al. | 310/12 |
| 2009/0070948 A1 * | 3/2009 | Bax | 15/22.2 |

* cited by examiner

*Primary Examiner* — Brian Glessner
*Assistant Examiner* — Brian D Mattei
(74) *Attorney, Agent, or Firm* — Ladas & Parry LLP

(57) ABSTRACT

A motorized toothbrush includes a shaft, a tooth brush mounted to a distal end of the shaft, a coil mounted to and surrounding the shaft, a first magnet adjacent to a periphery of the coil, and a second magnet adjacent to the periphery of the coil and on an opposite side of the coil with respect to the first magnet. Passing a current through the coil causes the shaft to rotate alternately clockwise and counterclockwise.

4 Claims, 6 Drawing Sheets

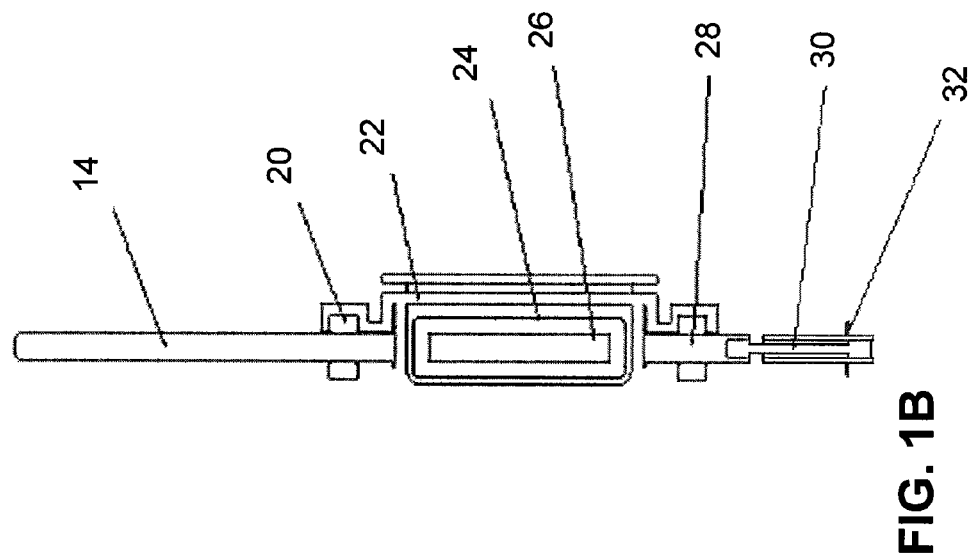
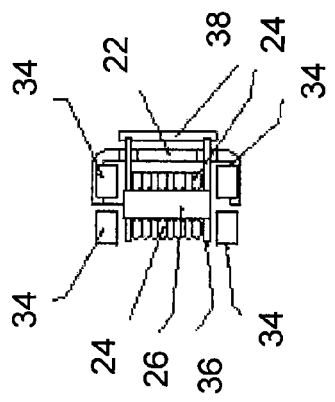
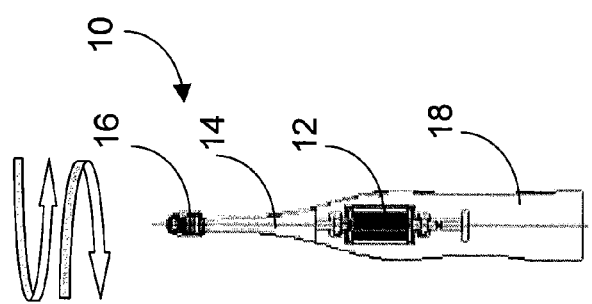
FIG. 1B
FIG. 1C
FIG. 1A

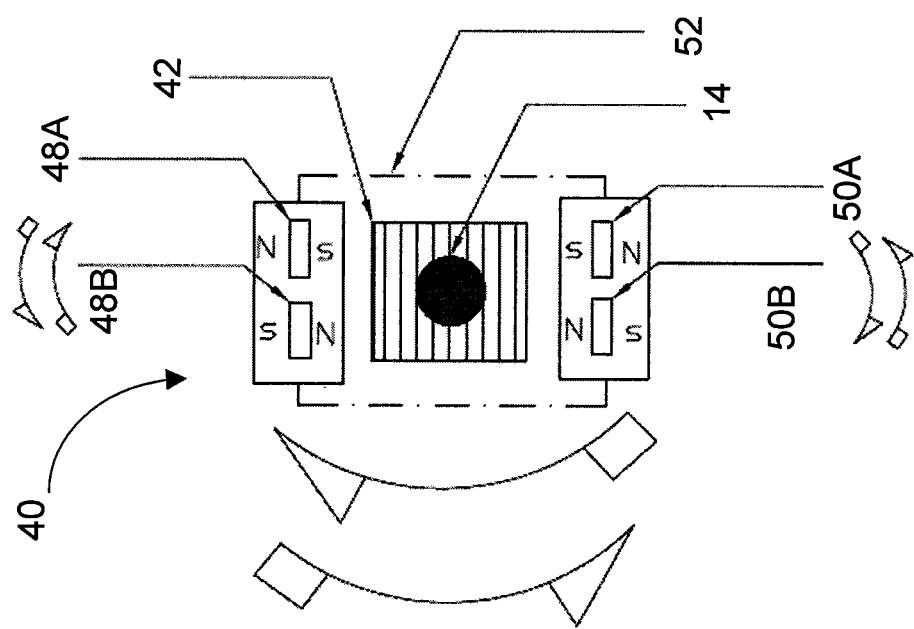

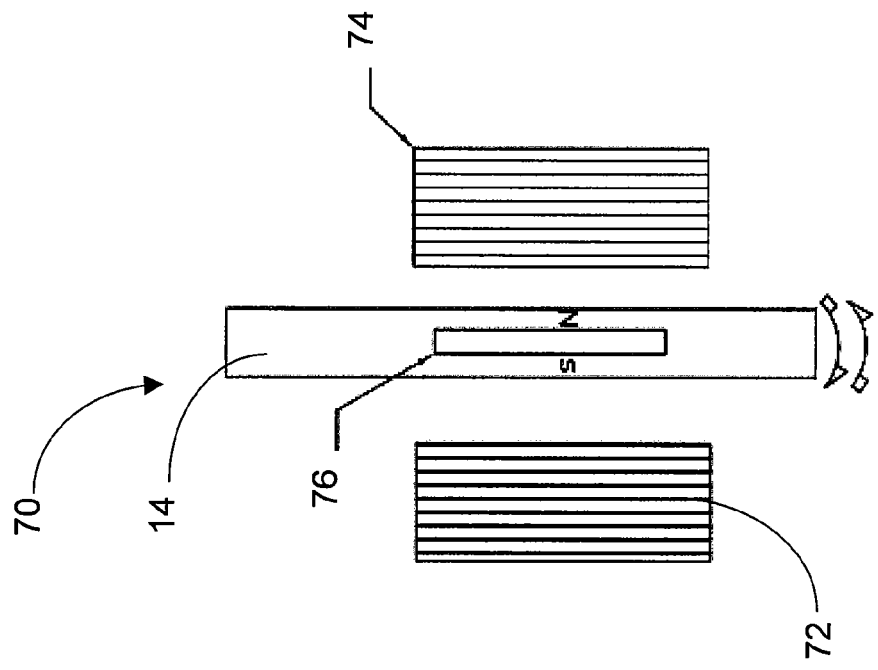
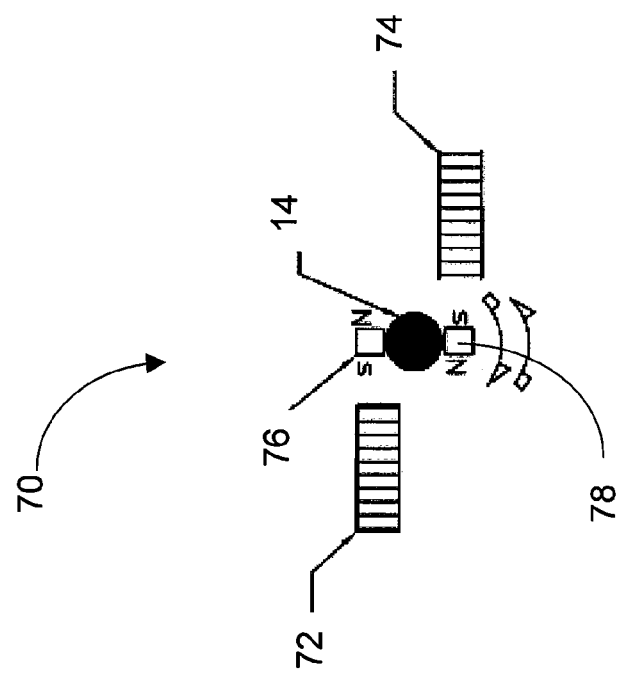
FIG. 4B
FIG. 4A

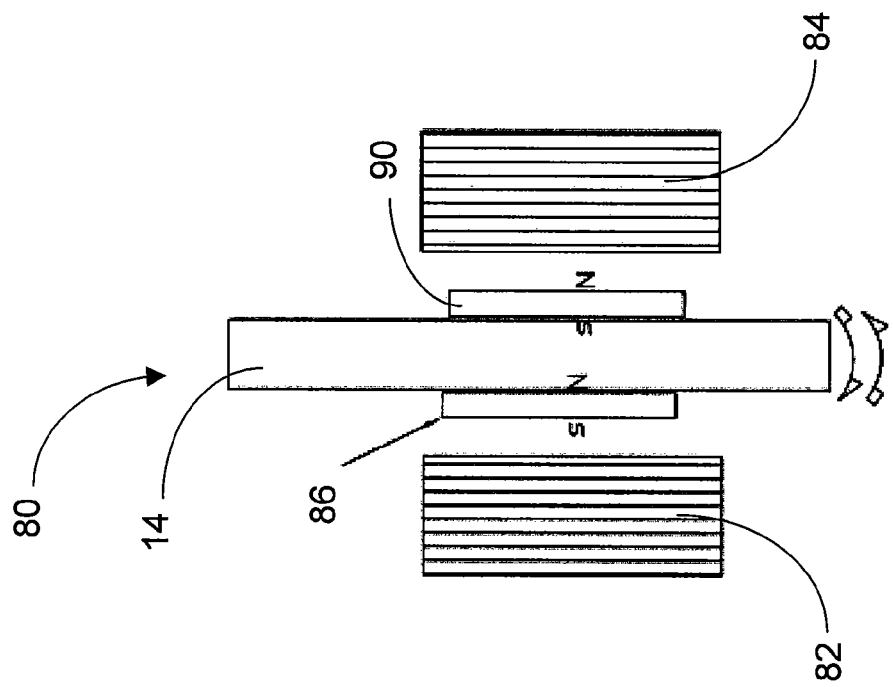
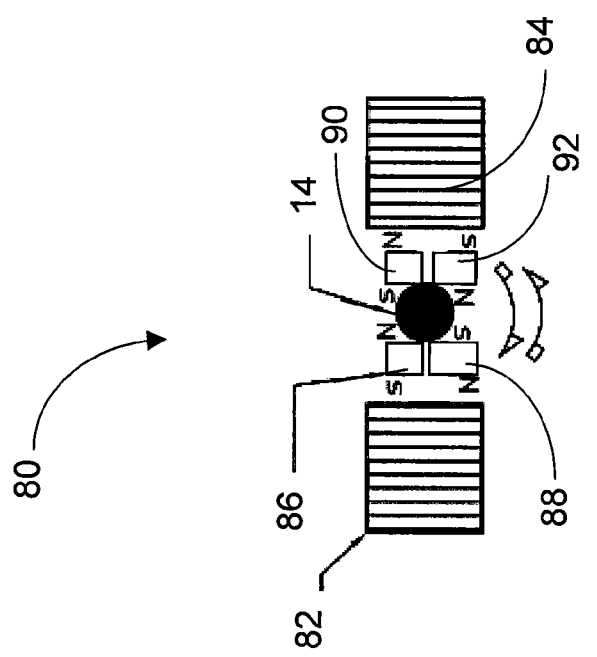

TOOTH BRUSH MOTOR

FIELD

This disclosure relates to tooth brushes and in particular to motors for motorized tooth brushes.

BACKGROUND

Motorized or powered toothbrushes are increasingly used by both adults and children. A desirable feature is a toothbrush with a clockwise and counterclockwise motion which, when the toothbrush is used, creates an up and down motion across a person's teeth.

What is needed are motors for motorized toothbrushes that have a cost effective design that are reliable and easy to manufacture. The embodiments of the present disclosure answer these and other needs.

SUMMARY

In a first embodiment disclosed herein, a motorized toothbrush comprises a shaft, a tooth brush mounted to a distal end of the shaft, a coil mounted to and surrounding the shaft, a first magnet adjacent to a periphery of the coil, and a second magnet adjacent to the periphery of the coil and on an opposite side of the coil with respect to the first magnet, wherein passing a current through the coil causes the shaft to rotate alternately clockwise and counterclockwise.

In another embodiment disclosed herein, a motorized toothbrush comprises a shaft, a tooth brush mounted to a distal end of the shaft, a first magnet mounted on a first side of the shaft, a second magnet mounted on the shaft on a side opposite the first side, a first coil adjacent to the first and second magnets such that a S orientation of the first magnet faces the first coil and a N orientation of the second magnet faces the first coil, and a second coil adjacent to the first and second magnets such that a N orientation of the first magnet faces the second coil and a S orientation of the second magnet faces the second coil, wherein a first current through the first coil causes a magnetic field in the first coil to interact with the first and second magnets, wherein a second current through the second coil causes a magnetic field in the second coil to interact with the first and second magnets, and wherein the first and second magnetic field interactions cause the shaft to rotate alternately clockwise and counterclockwise.

In another embodiment disclosed herein, a motorized toothbrush comprises a shaft, a tooth brush mounted to a distal end of the shaft, a first magnet mounted on a first side of the shaft, a second magnet mounted on the shaft on a side of the shaft opposite the first side, a first coil adjacent to the first magnet such that a S orientation of the first magnet faces the first coil, and a second coil adjacent to the second magnet such that a S orientation of the second magnet faces the second coil, wherein a first current through the first coil causes a magnetic field in the first coil to interact with the first magnet, wherein a second current through the second coil causes a magnetic field in the second coil to interact with the second magnet, and wherein the first and second magnetic field interactions cause the shaft to rotate alternately clockwise and counterclockwise.

In yet another embodiment disclosed herein, a motorized toothbrush comprises a shaft, a tooth brush mounted to a distal end of the shaft, a first magnet and a second magnet mounted on a first side of the shaft, a third magnet and a fourth magnet mounted on the shaft on a side of the shaft opposite the first side, a first coil adjacent to the first and second magnets such that a S orientation of the first magnet faces the first coil and a N orientation of the second magnet faces the first coil, and a second coil adjacent to the third and fourth magnets such that a N orientation of the third magnet faces the second coil and a S orientation of the fourth magnet faces the second coil, wherein a first current through the first coil causes a magnetic field in the first coil to interact with the first and second magnets, wherein a second current through the second coil causes a magnetic field in the second coil to interact with the third and fourth magnets, and wherein the magnetic field interactions of the first and second coil cause the shaft to rotate alternately clockwise and counterclockwise.

These and other features and advantages will become further apparent from the detailed description and accompanying figures that follow. In the figures and description, numerals indicate the various features, like numerals referring to like features throughout both the drawings and the description.

BRIEF DESCRIPTION OF THE DRAWINGS

FIGS. 1A-1C show a tooth brush in accordance with the present disclosure;

FIGS. 2A and 2B show a motor for a tooth brush in accordance with the present disclosure;

FIGS. 4A and 4B show another motor for a tooth brush in accordance with the present disclosure; and FIGS. 5A and 5B show another motor for a tooth brush in accordance with the present disclosure.

DETAILED DESCRIPTION

Figure 2A:
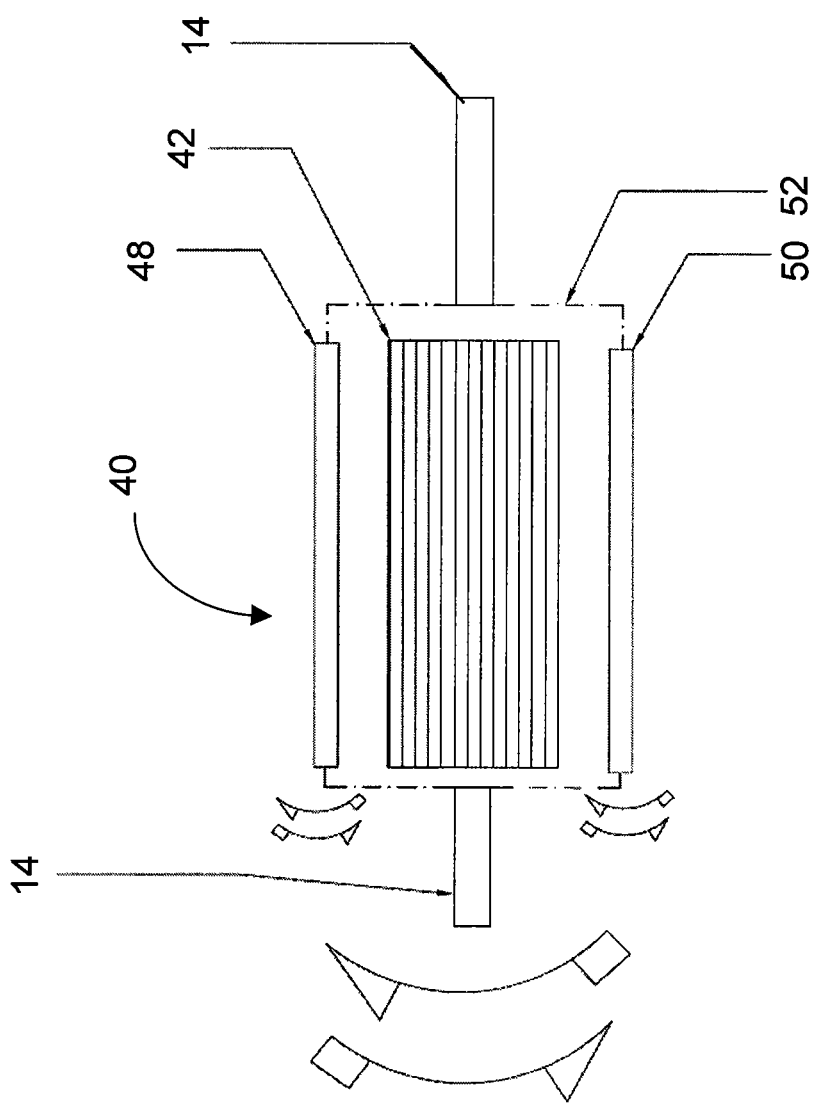

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

FIG. 1A shows a motorized tooth brush 10 in accordance with the present disclosure. A motor 12 is connect to a shaft 14 which drives a tooth brush 16 connected to a distal end of the shaft 14. The motor 12, shaft 14, and an electronic circuit (not shown) are held within enclosure 18. For brushing teeth, it is desirable that the shaft 14 and thereby the toothbrush 16 rapidly rotate alternately in a clockwise and counterclockwise motion, as shown in FIG. 1A.

FIG. 1B shows additional detail for the motorized toothbrush 10. A shaft 14 extends through bearing 20. A magnet holder 22 surrounds coil 24. Also included are silicone metal sheet 26, spring wire holder 28, spring wire 30, and spring wire fixture 32. On FIG. 1C magnets 34, silicone metal sheet guide 36, and silicone metal sheet holder 38 are shown.

FIGS. 2A and 2B show a motor 40 for a tooth brush in accordance with the present disclosure. In this embodiment a coil 42 is mounted to and surrounds shaft 14 to which the toothbrush 16 is connected. Magnets 48 and 50, which may be permanent magnets, are on opposite sides of the coil 42 and retained there by plastic enclosure 52, which may be attached to enclosure 18. The first magnet is mounted to enable at least a partial rotation of the first magnet. The second magnet is also mounted in a manner to enable at least a partial rotation of the second magnet.

An electronic circuit (not shown) generates a high frequency signal that passes current through the coil 42, which generates a magnetic field in the coil 42. The magnets 48 and 50 are rotated in an alternating clockwise and counterclockwise motion. The interaction of the coil 42 with the magnets 48 and 50 on opposite sides of the coil 42, causes a force which causes the shaft 14 to turn or rotate alternately clockwise and counter-clockwise. Thus the tooth brush 16 also turns alternately clockwise and counter-clockwise.

As shown in FIG. 2B, magnet 48 may have a N-S magnet 48A portion and a S-N magnet 48B portion. Similarly, magnet 50 may have a N-S magnet 50A portion and a S-N magnet 50B portion. Each of these may be permanent magnets.

Figure 3B:
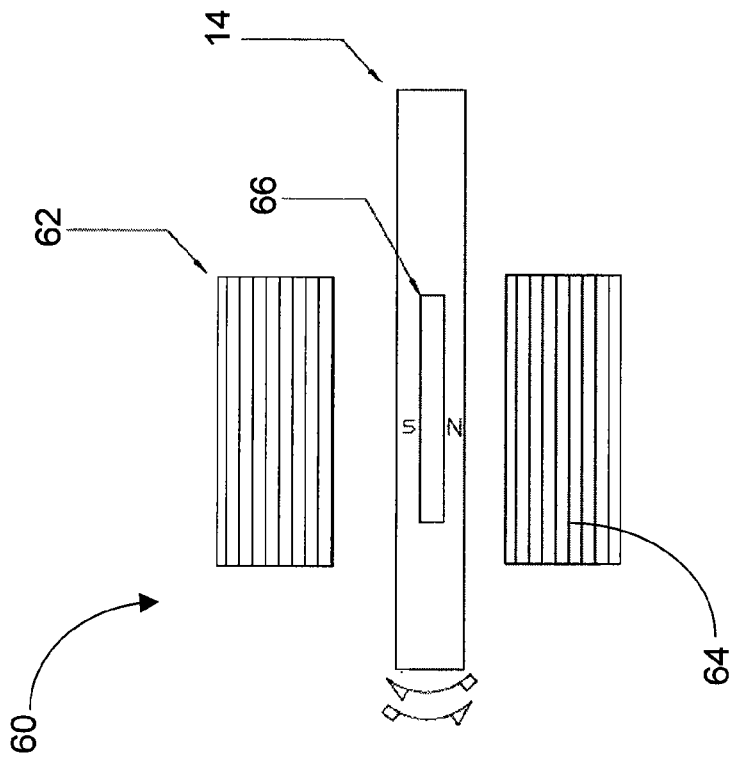
FIGS. 3A and 3B show another motor for a tooth brush in accordance with the present disclosure.
Figure 3A:
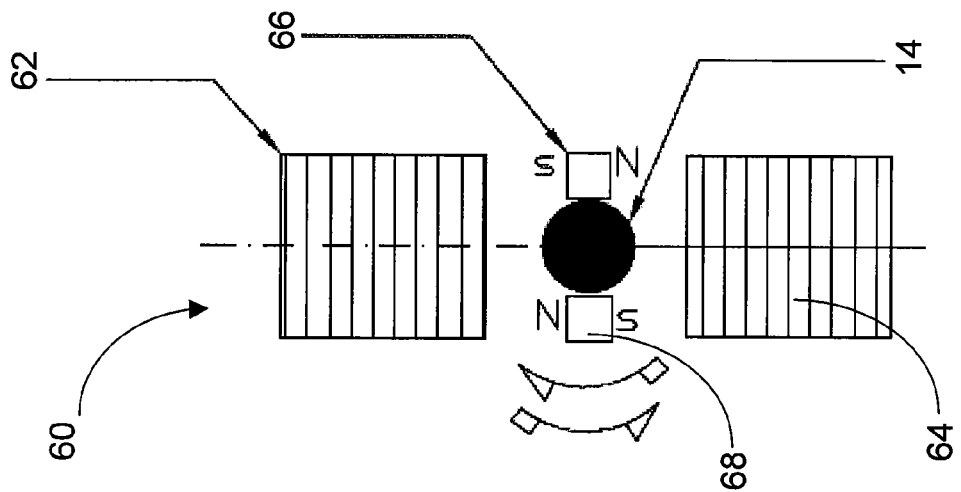

FIGS. 3A and 3B show another motor 60 for a tooth brush in accordance with the present disclosure. In this embodiment, magnets 66 and 68, which may be permanent magnets, are mounted on opposite sides of shaft 14. As shown the magnet 66 is mounted in a N-S manner and magnet 68 is mounted in an opposite S-N manner. A first coil 62 is on one side of the shaft 14 and a second coil 64 is on another side of the shaft, and the first coil 62 and second coil 64 are aligned relative to the magnets 66 and 68 such that both magnet 66 and magnet 68 interact with both the first coil 62 and the second coil 64. Enclosure 18 may be configured to retain the first coil 62 and second coil 64 relative to the magnets 66 and 68 mounted on the shaft 14.

An electronic circuit (not shown) generates a high frequency signal that passes a current through first coil 62 and a current through second coil 64. The current generates a magnetic field in the first coil 62 and a magnetic field in the second coil 64. The generated magnetic fields alternate so that the magnetic field changes from a north (N) to a south (S) orientation at frequency of the alternating high frequency signal. The magnetic field of the first coil 62 interacts with the magnets 66 and 68 on opposite sides of the shaft 14. The magnetic field of the second coil 64 also interacts with the magnets 66 and 68 on opposite sides of the shaft 14. These interactions cause forces which cause the shaft 14 to turn or rotate alternately clockwise and counter-clockwise. Thus the tooth brush 16 also turns alternately clockwise and counter-clockwise.

FIGS. 4A and 4B show yet another motor 70 for a tooth brush in accordance with the present disclosure. As shown, magnets 76 and 78, which may be permanent magnets, are mounted on opposite sides of shaft 14. The magnet 76 is mounted in a N-S manner and the magnet 78 is mounted in an opposite S-N manner. A first coil 72 is oriented adjacent magnet 76. A second coil 74 is oriented adjacent magnet 78. Enclosure 18 may be configured to retain the coils 72 and 74 adjacent to the magnets 76 and 78, respectively.

An electronic circuit (not shown) generates a high frequency signal that passes current through the first coil 72. The electronic circuit also generates an alternating high frequency signal that passes current through the second coil 74. The current generates a magnetic field in the first coil 72, which alternates so that the magnetic field changes from a north (N) to a south (S) orientation at frequency of the alternating high frequency signal. The magnetic field of coil 72 interacts with the magnet 76. A magnetic field is also generated in the second coil 74, which alternates so that the magnetic field changes from a north (N) to a south (S) orientation at frequency of the alternating high frequency signal. The magnetic field of coil 74 interacts with the magnet 78. These interactions cause forces which cause the shaft 14 to turn or rotate alternately clockwise and counter-clockwise. Thus the tooth brush 16 also turns alternately clockwise and counter-clockwise.

FIGS. 5A and 5B show another motor 80 for a tooth brush in accordance with the present disclosure. In this embodiment, magnets 86 and 88, which may be permanent magnets, are mounted on one side of shaft 14, and magnets 90 and 92, which may also be permanent magnets, are mounted on an opposite side of shaft 14. As shown, the magnet 86 is mounted in a S-N manner and magnet 88 is mounted in an opposite N-S manner. A first coil 82 is on one side of the shaft 14 and aligned relative to the magnets 86 and 88 such that both magnet 86 and magnet 88 interact with first coil 82. Further, as shown in FIG. 5A, the magnet 90 is mounted in a S-N manner and magnet 92 is mounted in an opposite N-S manner. A second coil 84 is on a side of the shaft 14 opposite to the side that first coil 82 is on and is aligned relative to the magnets 90 and 92 such that both magnet 90 and magnet 92 interact with second coil 84. Enclosure 18 may be configured to retain the first coil 82 adjacent to the magnets 86 and 88 and to retain the second coil 84 adjacent to the magnets 90 and 92.

An electronic circuit (not shown) generates a high frequency signal that passes a current through first coil 82 and a current through second coil 84. The current generates a magnetic field in the first coil 82. A magnetic field is also generated in the second coil 84. The generated magnetic fields alternate so that the magnetic field changes from a north (N) to a south (S) orientation at frequency of the high frequency signal. The magnetic field of the first coil 82 interacts with the magnets 86 and 88. The magnetic field of the second coil 84 interacts with the magnets 90 and 92. These interactions cause forces which cause the shaft 14 to turn or rotate alternately clockwise and counter-clockwise. Thus the tooth brush 16 also turns alternately clockwise and counter-clockwise.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

What is claimed is:

1. A motorized toothbrush comprising:
   a shaft;
   a tooth brush mounted to a distal end of the shaft;
   a coil mounted to and surrounding the shaft;
   a first magnet adjacent to a periphery of the coil; and
   a second magnet adjacent to the periphery of the coil and on an opposite side of the coil with respect to the first magnet;
   wherein passing a current through the coil causes the shaft and the coil mounted thereto to rotate alternately clockwise and counterclockwise around the axis of the shaft;
   wherein the first magnet adjacent to the periphery of the coil is configured to at least partially rotate alternately clockwise and counterclockwise without being coupled to the coil rotation;
   wherein the second magnet adjacent the periphery of the coil is configured to at least partially rotate alternately clockwise and counterclockwise without being coupled to the coil rotation;
   the first magnet comprises a first N-S portion nearer the coil and a first S-N portion further away from the coil;
   the second magnet comprises a second N-S portion nearer the coil and a second S-N portion further away from the coil;
   wherein the first N-S portion is opposite the second N-S portion; and
   wherein the first S-N portion is opposite the second S-N portion.

2. The motorized toothbrush of claim 1 wherein:
   wherein passing a current through the coil and rotating the first magnet and the second magnet alternately clockwise and counterclockwise causes the shaft to rotate alternately clockwise and counterclockwise.

3. The motorized toothbrush of claim 1 wherein:
   the first magnet comprises a permanent magnet; and
   the second magnet comprises a permanent magnet.

4. The motorized toothbrush of claim 1 further comprising;
   an enclosure for retaining the first magnet adjacent to a periphery of the coil and retaining the second magnet adjacent to the periphery of the coil.

* * * * *